United States Patent [19]
Strom et al.

[11] Patent Number: 6,133,034
[45] Date of Patent: Oct. 17, 2000

[54] METHODS AND COMPOSITIONS RELATED TO THE PRODUCTION OF TREHALOSE

[75] Inventors: Arne Reidar Strom; Inga Kaasen; Olaf Bay Styrvold; John McDougall, all of Tromso, Norway

[73] Assignee: Calgene, Inc., Davis, Calif.

[21] Appl. No.: 08/274,121

[22] Filed: Jul. 12, 1994

Related U.S. Application Data

[63] Continuation of application No. 07/893,099, May 27, 1992, abandoned.
[51] Int. Cl.$^7$ .............................. C12N 5/04; C12N 15/31; C12N 15/63; C12N 15/82
[52] U.S. Cl. ...................... 435/419; 435/69.1; 435/70.1; 435/172.3; 435/320.1; 435/410; 435/71.1; 435/183; 536/23.2; 536/23.7; 536/24.1; 800/205
[58] Field of Search ................................. 435/69.1, 70.1, 435/71.1, 172.3, 320.1, 183, 240.4, 240.49, 410, 419; 536/23.1, 23.2, 23.7, 24.1; 800/2, 205

[56] References Cited

U.S. PATENT DOCUMENTS

| | | | |
|---|---|---|---|
| 4,806,343 | 2/1989 | Carpenter et al. | 424/450 |
| 4,857,319 | 8/1989 | Crowe et al. | 424/94.1 |
| 4,891,319 | 1/1990 | Roser | 435/188 |
| 5,026,566 | 6/1991 | Roser | 426/443 |
| 5,422,254 | 6/1995 | Londesborough et al. | 435/97 |

FOREIGN PATENT DOCUMENTS

WO 90/10076  9/1990  WIPO.

OTHER PUBLICATIONS

Eleanor White et al., Comparative Biochemestry of the Lycopods, Phytochemistry (1967), pp. 663–667.
Otto Kandler, Biosynthesis of Poly– and Oligosaccharides During Photosynthesis in Green Plants, Harvesting the Sun: Photosynthesis In Plant Life (1967), pp. 131–152.
K. Veluthambi et al., Cell Wall Synthesis Is Inhibited Upon Trehalose Feeding, Plant Physiol. (1982) 70, pp. 686–688.
R. M. Roberts et al., Trehalase Activity in *Selaginella Martensii*, Archives of Biochemistry and Biophysics 133 (1969), pp. 408–412.
Herbert Hop et al., Physiology of Unbelliferose, Biochem. Physiol. Pflanzen 169 (1976), pp. 5–36.
Manfred Fischer et al., Identifizierung Von Selaginoze und Deren Verbreitung in der Gattung Selaginella, Phytochemistry (1975) vol. 14, pp. 2629–2633.
K. Veluthambi et al., Correlation With Low Trehalas Activity, Plant Physiol. (1981) 68, pp. 1369–1374.
O. Kandler et al., Vorkommen Von Trehalose In *Botrychium lunaria*, Z. Pflanzenphysiol. Bd. 53 (1965), pp. 157–161.
Erika Löhr, Trehalose, Respiration und Photosynthese in Dem Farn Ophioglossum. Ein Neuer Schattenblattypus, Physiologia Plantarum (1968) vol. 21, pp. 668–672.
Arnold E. S. Gussin, Does Trehalose Occur in Angiospermae?, Phytochemistry vol. 11 (1972) pp. 1827–1828.

Franz Oesch et al., Trehalose in the Cambial Sap of *Fagus Silvatica* L., Phytochemistry vol. 6, (1967), pp. 1147–1148.
Attfield, Paul V., "Trehalose accumulates in *Saccharomyces cerevisiae* during exposure to agents that induce heat shock response," FEBS (1987) 225(1,2) :259–263.
Bell, et al., "Characterization of the 56–kDa subunit of yeast Trehalose–6–phosphate synthase and cloning of its gene reveal its identity with the product of CIF1, a regulator of carbon catabolite inactivation," Eur. J. Biochem. (1992) 209:951–959.
Glaever, et al., "Biochemical and Genetic Characterization of Osmoregulatory Trehalose Synthesis in *Escherichia coli*," J. of Bacteriology (1988) 170(6) :2841–2849.
Gutierrez, et al., "Analysis and DNA sequence of the osmoregualated treA gene encoding the periplasmic trehalase of *Escherichia coli* K12," Mol.Gen.Genet. (1989) 217:347–354.
Hendrickson, et al., "Physical Map Location of the argFGH Operon of *Escherichia coli*," J. Bacteriology (1992) 174(11) :3836–3837.
Hengge–Aronis, et al., "Trehalose Synthesis Genes Are Controlled by the Putative Sigma Factor Encoded by ropS and Are Involved in Stationary–Phase Thermotolerance in *Escherichia coli*," J. Bacteriology (1991) 173(24) :7918–7924.
Hino, et al., "Trehalose Levels and Survival Ratio of Freeze–Tolerant vers Freeze–Sensitive Yeasts," App. and Env. Microbiology (1990) 56:1386–1391.
Hottiger, et al., "Rapid changes of heat and desiccation tolerance correlated with changes of trehalose content in *Saccharomyces cerevisiae* cells subjected to temperature shifts," FEBS (1987) 220(1) :113–115.
Kaasen, et al., "Molecular Cloning and Physical Mapping of the otsBA Genes, Which Encode the Osmoregulatory Trehalose Pathway of *Escherichia coli*: Evidence that Transcription Is Activated by KatF (AppR)," J. Bacteriology (1992) 174(3) :889–898.
Klein, et al., "The repression of trehalose transport and metabolism in *Escherichia coli* by high osmolarity is mediated by Trehalose–6–phosphate phosphatase," Res. Microbiol. (1991) 142:359–371.
Levine, et al., "Another View of Trehalose for Drying and Stabilizing Biological Materials," BioPharm (1992) 36–40.
Londesborough, et al., "Trehalose–6–phosphate synthase/phosphatase complex from bakers' yeast: purification of a proteolytically activated form," J. Gen. Microbiol. (1991) 137:323–330.

(List continued on next page.)

Primary Examiner—David T. Fox
Assistant Examiner—Elizabeth C. Kemmerer
Attorney, Agent, or Firm—Carl J. Schwedler

[57] ABSTRACT

This invention relates to genes involved in the biosynthesis of trehalose. The genes encode trehalose-6-phosphate synthase (trehalose synthase) and trehalose-6-phosphate phosphatase (trehalose phosphatase).

19 Claims, 13 Drawing Sheets

OTHER PUBLICATIONS

Nelson, et al., "A Conserved Gene Encoding the 57–kDa Subunit of the Yeast Vacuolar H⁺–ATPase," *J. Biol. Chem.* (1989) 264(3) :1775–1778.

Rod, et al., "Accumulation of Trehalose by *Escherichia coli* K–12 at High Osmotic Pressure Depends on the Presence of Amber Suppressors," *J. of Bacteriology* (1988) 170(8) :3601–3610.

Ruf, et al., "Rabbit Small Intestinal Trehalase," *J. Biol. Chem.* (1990) 265(25) :15034–15039.

Scripture, et al., "High–affinity L–Arabinose Transport Operon Nucleotide Sequence and Analysis of Gene Products," *J. Mol. Biol.* (1987) 197:37–46.

Strom, et al., "Genetics of osmoregulation in *Escherichia coli*: uptake and biosynthesis of organic osmolytes," *FEMS Microbiology Reviews* (1986) 39:79–86.

Styrvold, et al., "Synthesis, Accumulation and Excretion of Trehalose in Osmotically Stressed *Escherichia coli* K–12 Strains: Influence of Amber Suppressors and Function of the Periplasmic Trehalase," *J. Bacteriology* (1991) 173(3) :1187–1192.

Glaever et al. 1988. J Bacteriol 170: 2841–2849.

Rogers et al. 1987. Meth Enzymol. 153D: 253–277.

Georges et al. 1990. Gene 91:159–165.

Hino et al. 1990 Appl. Env. Microbiol. 56:1386–1391.

Kaasen et al. 1992. J Bacteriol. 174: 889–898.

McBride et al. 1990. Plant Mol. Biol. 14: 259–276.

Hoekema et al. 1980. Nature 303: 179–180.

Larkins et al. 1985. J. Cell. Biochem. Suppl. 0(9 Part C):264.

Finnegan et al. 1994. Bio/Technology 12: 883–888.

Keith et al. 1986. EMBO J. 5: 2419–25.

Lee et al. 1990. J. Cell. Biochem., Suppl. 14E, p. 303.

```
   A AGC TTC TTT GCC CTT GGT TAC GCC AAC TGG TTC GGT CTG CCT GCG CCA
     Ser Phe Phe Ala Leu Gly Tyr Ala Asn Trp Phe Gly Leu Pro Ala Pro
50
ATC TGG CTC ACC GTC GCG TGT CTG ATT ATC TTT GGT TTG CTG CTG AAT
Ile Trp Leu Thr Val Ala Cys Leu Ile Ile Phe Gly Leu Leu Leu Asn
100
AAA ACC ACC TTT GGT CGT AAC ACC CTG GCG ATT GGC GGG AAC GAA GAG
Lys Thr Thr Phe Gly Arg Asn Thr Leu Ala Ile Gly Gly Asn Glu Glu
     150
GCC GCG CGT CTG GCG GGT GTA CCG GTT GTT CGC ACC AAA ATT ATT ATC
Ala Ala Arg Leu Ala Gly Val Pro Val Val Arg Thr Lys Ile Ile Ile
          200
TTT GTT CTC TCA GGC CTG GTA TCA GCG ATA GCC GGA ATT ATT CTG GCT
Phe Val Leu Ser Gly Leu Val Ser Ala Ile Ala Gly Ile Ile Leu Ala
               250
TCA CGT ATG ACC AGT GGG CAG CCA ATG ACG TCG ATT GGT TAT GAG CTG
Ser Arg Met Thr Ser Gly Gln Pro Met Thr Ser Ile Gly Tyr Glu Leu
                    300
ATT GTT ATC TCC GCC TGC GTT TTA GGT GGC GTT TCT CTG AAA GGT GGC
Ile Val Ile Ser Ala Cys Val Leu Gly Gly Val Ser Leu Lys Gly Gly
```

FIGURE 1A

```
         350
ATC GGA AAA ATC TCA TAT GTG GTG GCG GGT ATC TTA ATT TTA GGC ACC
Ile Gly Lys Ile Ser Tyr Val Val Ala Gly Ile Leu Ile Leu Gly Thr
             400
GTG GAA AAC GCC ATG AAC CTG CTT AAT ATT TCT CCT TTC GCG CAG TAC
Val Glu Asn Ala Met Asn Leu Leu Asn Ile Ser Pro Phe Ala Gln Tyr
                     450
GTG GTT CGC GGC TTA ATC CTG CTG GCA GCG GTG ATC TTC GAC CGT TAC
Val Val Arg Gly Leu Ile Leu Leu Ala Ala Val Ile Phe Asp Arg Tyr
                         500
AAG CAA AAA GCG AAA CGC ACT GTC TGATG CTTTTTTCTG CAACAATTTA
Lys Gln Lys Ala Lys Arg Thr Val
                 550
GCGTTTTTTC CCACCATAGC CAACCGCCAT AACGGTTGGC TGTTCTTCGT TGCAAATGGC
                                                              650
     600
GACCCCCGTC ACACTGTCTA TACTTACATG TCTGTAAAGC GCGTTCTGCG CAACACAATA
                                                              700
AGAAAAGAGA AGGAGGAGAA CCGG GTG ACA GAA CCG TTA ACC GAA ACC CCT GAA
                          Val Thr Glu Pro Leu Thr Glu Thr Pro Glu
```

FIGURE 1B

```
CTA TCC GCG AAA TAT GCC TGG TTT TTT GAT CTT GAT GGA ACG CTG GCG
Leu Ser Ala Lys Tyr Ala Trp Phe Phe Asp Leu Asp Gly Thr Leu Ala
                                                        750
                                                                    800
GAA ATC AAA CCG CAT CCC GAT CAG GTC GTC CCT GAC AAT ATT CTG
Glu Ile Lys Pro His Pro Asp Gln Val Val Pro Asp Asn Ile Leu

CAA GGA CTA CAG CTA CTG GCA ACC GCA AGT GAT GGT GCA TTG GCA TTG
Gln Gly Leu Gln Leu Leu Ala Thr Ala Ser Asp Gly Ala Leu Ala Leu
850
ATA TCA GGG CGC TCA ATG GTG GAG CTT GAC GCA CTG GCA AAA CCT TAT
Ile Ser Gly Arg Ser Met Val Glu Leu Asp Ala Leu Ala Lys Pro Tyr
    900
CGC TTC CCG TTA GCG GGC GTG CAT GGG GCG GAG CGC CGT GAC ATC AAT
Arg Phe Pro Leu Ala Gly Val His Gly Ala Glu Arg Arg Asp Ile Asn
            950
GGT AAA ACA CAT ATC GTT CAT CTG CCG GAT GCG ATT GCG CGT GAT ATT
Gly Lys Thr His Ile Val His Leu Pro Asp Ala Ile Ala Arg Asp Ile
                1000
AGC GTG CAA CTG CAT ACA GTC ATC GCT CAG TAT CCC GGC GCG GAG TGG
Ser Val Gln Leu His Thr Val Ile Ala Gln Tyr Pro Gly Ala Glu Trp
```

FIGURE 1C

```
                                                 1050
GAG GCG AAA GGG ATG GCT TTT GCG CTG CAT TAT CGT CAG GCT CCG CAG
Glu Ala Lys Gly Met Ala Phe Ala Leu His Tyr Arg Gln Ala Pro Gln

1100
CAT GAA GAC GCA TTA ATG ACA TTA GCG CAA CGT ATT ACT CAG ATC TGG
His Glu Asp Ala Leu Met Thr Leu Ala Gln Arg Ile Thr Gln Ile Trp

1150
CCA CAA ATG GCG TTA CAG CAG GGA CAG AAG TGT GTT GTC GAG ATC AAA CCG
Pro Gln Met Ala Leu Gln Gln Gly Gln Lys Cys Val Val Glu Ile Lys Pro

1200
AGA GGT ACC AGT AAA GGT GAG GCA ATT GCA GCT TTT ATG CAG GAA GCT
Arg Gly Thr Ser Lys Gly Glu Ala Ile Ala Ala Phe Met Gln Glu Ala

1250
CCC TTT ATC GGG CGA ACG CCC GTA TTT CTG GGC GAT GAT TTA ACC GAT
Pro Phe Ile Gly Arg Thr Pro Val Phe Leu Gly Asp Asp Leu Thr Asp

1300
GAA TCT GGC TTC GCA GTC GTT AAC CGA CTG GGC GGA ATG TCA GTA AAA
Glu Ser Gly Phe Ala Val Val Asn Arg Leu Gly Gly Met Ser Val Lys

1350
ATT GGC ACA GGT GCA ACT CAG CAG GCA TCA TGG CGA CTG GCG GGT GTG CCG
Ile Gly Thr Gly Ala Thr Gln Gln Ala Ser Trp Arg Leu Ala Gly Val Pro
```

FIGURE 1D

```
GAT GTC TGG AGC TGG CTT GAA ATG ATA ACC ACC GCA TTA CAA CAA AAA
Asp Val Trp Ser Trp Leu Glu Met Ile Thr Thr Ala Leu Gln Gln Lys
                      1400                          1450
AGA GAA AAT AAC AGG AGT GAT GAC TAT GAG TCG TTT AGT CGT AGT ATC T
Arg Glu Asn Asn Arg Ser Asp Asp Tyr Glu Ser Phe Ser Arg Ser Ile
                                    Met Thr Met Ser Arg Leu Val Val Ser
AAC CGG ATT GCA CCA GAC CAC GAG CAC GCC GCC AGT GCC GGT GGC CTT
Asn Arg Ile Ala Pro Asp His Glu His Ala Ala Ser Ala Gly Gly Leu
                              1500                          1550
GCC GTT GGC ATA CTG GGG GCA CTG AAA GCC GCA GGC GGA CTG TGG TTT
Ala Val Gly Ile Leu Gly Ala Leu Lys Ala Ala Gly Gly Leu Trp Phe
                                              1600
GGC TGG AGT GGT GAA ACA GGG AAT GAG GAT CAG CCG CTA AAA AAG GTG
Gly Trp Ser Gly Glu Thr Gly Asn Glu Asp Gln Pro Leu Lys Lys Val
                                                          1650
AAA AAA GGT AAC ATT ACG TGG GCC TCT TTT AAC CTC AGC GAA CAG GAC
Lys Lys Gly Asn Ile Thr Trp Ala Ser Phe Asn Leu Ser Glu Gln Asp
```

FIGURE 1E

```
                                                        1700
CTT GAC GAA TAC TAC AAC CAA TTC TCC AAT GCC GTT CTC TGG CCC GCT
Leu Asp Glu Tyr Tyr Asn Gln Phe Ser Asn Ala Val Leu Trp Pro Ala

1750
TTT CAT TAT CGG CTC GAT CTG CAA TTT CAG CGT CCT GCC TGG GAC
Phe His Tyr Arg Leu Asp Leu Val Gln Phe Gln Arg Pro Ala Trp Asp

1800
GGC TAT CTA CGC GTA AAT GCG TTG CTG GCA GAT AAA TTA CTG CCG CTG
Gly Tyr Leu Arg Val Asn Ala Leu Leu Ala Asp Lys Leu Leu Pro Leu

1850
TTG CAA GAC GAT GAT ATT ATC TGG ATC CAC GAT TAT CAC CTG TTG CCA
Leu Gln Asp Asp Asp Ile Ile Trp Ile His Asp Tyr His Leu Leu Pro

1900
TTT GCG CAT GAA TTA CGC AAA CGG GGA GTG AAT CGC GAA ATC TTC TTC
Phe Ala His Glu Leu Arg Lys Arg Gly Val Asn Arg Glu Ile Gly Phe

1950
TTT CTG CAT ATT CCT TTC CCG ACA CCG GAA ATC TTC AAC GCG CTG CCG
Phe Leu His Ile Pro Phe Pro Thr Pro Glu Ile Phe Asn Ala Leu Pro

2000
ACA TAT GAC ACC TTG CTT GAA CAG CTT TGT GAT TAT GAT TTG CTG GGT
Thr Tyr Asp Thr Leu Leu Glu Gln Leu Cys Asp Tyr Asp Leu Leu Gly

FIGURE 1F
```

```
TTC CAG ACA GAA AAC GAT CGT CTG GCG TTC CTG GAT TGT CTT TCT AAC
Phe Gln Thr Glu Asn Asp Arg Leu Ala Phe Leu Asp Cys Leu Ser Asn
2050
CTG ACC CGC GTC ACG ACA CGT AGC GCA AAA AGC CAT ACA GCC TGG GGC
Leu Thr Arg Val Thr Thr Arg Ser Ala Lys Ser His Thr Ala Trp Gly
2100
AAA GCA TTT CGA ACA GAA GTC TAC CCG ATC GGC ATT GAA CCG AAA GAA
Lys Ala Phe Arg Thr Glu Val Tyr Pro Ile Gly Ile Glu Pro Lys Glu
    2150
ATA GCC AAA CAG GCT GCC GGG CCA CTG CCG CCA AAA CTG GCG CAA CTT
Ile Ala Lys Gln Ala Ala Gly Pro Leu Pro Pro Lys Leu Ala Gln Leu
         2200
AAA GCG GAA CTG AAA AAC GTA CAA AAT ATC TTT TCT GTC GAA CGG CTG
Lys Ala Glu Leu Lys Asn Val Gln Asn Ile Phe Ser Val Glu Arg Leu
              2250
GAT TAT TCC AAA GGT TTG CCA GAG CGT TTT CTC GCC TAT GAA GCG TTG
Asp Tyr Ser Lys Gly Leu Pro Glu Arg Phe Leu Ala Tyr Glu Ala Leu
         2300
CTG GAA AAA TAT CCG CAG CAT GGT AAA ATT CGT TAT ACC CAG ATT
Leu Glu Lys Tyr Pro Gln His Gly Lys Ile Arg Tyr Thr Gln Ile
```

FIGURE 1G

```
GCA CCA ACG TCG CGT GGT GAT GTG CAA GCC TAT CAG GAT ATT CGT CAT
Ala Pro Thr Ser Arg Gly Asp Val Gln Ala Tyr Gln Asp Ile Arg His
        2350                          2400
CAG CTC GAA AAT GAA GCT GGA CGA ATT AAT GGT AAA TAC GGG CAA TTA
Gln Leu Glu Asn Glu Ala Gly Arg Ile Asn Gly Lys Tyr Gly Gln Leu
                    2450
GGC TGG ACG CCG CTT TAT TAT TTG AAT CAG CAT TTT GAC CGT AAA TTA
Gly Trp Thr Pro Leu Tyr Tyr Leu Asn Gln His Phe Asp Arg Lys Leu
                            2500
CTG ATG AAA ATA TTC CGC TAC TCT GAC GTG GGC TTA GTG ACG CCA CTG
Leu Met Lys Ile Phe Arg Tyr Ser Asp Val Gly Leu Val Thr Pro Leu
                                    2550
CGT GAC GGG ATG AAC CTG GTA GCA AAA GAG TAT GTT GCT GCT CAG GAC
Arg Asp Gly Met Asn Leu Val Ala Lys Glu Tyr Val Ala Ala Gln Asp
                                            2600
CCA GCC AAT CCG GGC GTT CTT GTT CTT TCG CAA TTT GCG GGA GCG GCA
Pro Ala Asn Pro Gly Val Leu Val Leu Ser Gln Phe Ala Gly Ala Ala
                                                    2650
AAC GAG TTA ACG TCG GCG TTA ATT GTT AAC CCC TAC GAT CGT GAC GAA
Asn Glu Leu Thr Ser Ala Leu Ile Val Asn Pro Tyr Asp Arg Asp Glu
```

FIGURE 1H

```
GTT GCA GCT GCG CTG GAT CGT GCA TTG ACT ATG TCG CTG GCG GAA CGT
Val Ala Ala Ala Leu Asp Arg Ala Leu Thr Met Ser Leu Ala Glu Arg
                        2700

ATT TCC CGT CAT GCA GAA ATG CTG GAC GTT ATC GTG AAA AAC GAT ATT
Ile Ser Arg His Ala Glu Met Leu Asp Val Ile Val Lys Asn Asp Ile
                2750

AAC CAC TGG CAG GAG TGC TTC ATT AGC GAC CTA AAG CAG ATA GTT CCG
Asn His Trp Gln Glu Cys Phe Ile Ser Asp Leu Lys Gln Ile Val Pro
                            2800

CGA AGC GCG GAA AGC CAG CAG CGC GAT AAA GTT GCT ACC TTT CCA AAG
Arg Ser Ala Glu Ser Gln Gln Arg Asp Lys Val Ala Thr Phe Pro Lys
                                2850

CTT
Leu
```

FIGURE 1I

```
RF1    1   gamdklhxgskthvllxvciyrerlrrtrvvgrdxltwxsylvnxvsvsflleqarsxvsn

RF1   62   kagxqtryshtdllrhrtMTtdnakaqltsssggniiVVSNRlpvtitkkqqygtvrvtqc
                              *           ||
                              MT                            MT
OTSA   1                                     msrlvVVSNR       iappdehaas
                                                 |||||
RF1  123   rpeaghGvgrveedvhfqWFGWpGleipdDekdqvrkdllekfnavpiflsDeiEtYttg
                         ||||                                  ||||
OTSA  23   agglavGilgalkaagglWFGWsGetgneDqplkkvKkgnitwasfnlseqDldEyYnqfs RF1  184   svilfygrysitiLVrsistrmrgsDnakaqhqtftneiaktmnhnDlIWvHDYHLmlvpe
                        ||              |              |||||||||
OTSA  84   navLwpafhyrldLV    qfqrpawDgylrvnalladkllpllqddDiIWiHDYHLlpfah RF1  245   mLRvkiheKqlqNvkvGwFLHtPFPssEIyrilPvrqeilkgvlscDLvGFhTydyarhFL
            ||      |   |  | ||| |||  ||   |  |       ||  ||    ||
OTSA 142           KrgvNnriGfFLHiPFPtpEIfnaLPtydtlLeqlcdyDLlGFqTendrlaFL RF1  306   ssvqrvlnVnTlpngveyradsltxgpslsvstwtsspmgxkrnPykresnnxrklsraar
                    *                                  |
OTSA 198   dclsnltrVtTrsakshtawgkafrtevypigiepkeiakqaagPlppklaqlkaelknvq
```

FIGURE 2A-1

```
RF1   367  sxlvstgwitSKvcPqklhAmEvfLnehPewrGKvvlvQvAvpSRGDVeeYQylRsvvnel
                     ||  |    | |  |   |   ||    | |  |||||  ||  |
OTSA  259  nifsverldySKglPerflAyEalLekyPqhhGKirytQiAptSRGDVqaYQdiRhqlene RF1   428  vGRItvssvlwnsspsisctslyhlksxfrymlxamfvwsrppvmvxtwfptnillakkkr
            |||
OTSA  320  aGRI RF1   489  kvpxsxvssqvphnpxmvlllxilgTPmiflmpstrpxlcpmxRKkltgknftntslntLL
                                    ||                ||              ||
OTSA  324                  ngkygqlgwTP       lyylnqhfdRK              LL RF1   550  psgvKIssmnytvhhqaqqaPLppktdepdAKxddrlflvrfslpslLftFfttlykiixm
               ||              ||        ||               |  |
OTSA  348     mKI    frysdvglvtPL rdgmnlvAKeyvaaqdpanpgvlvLsqFagaaneltsa RF1   611  txlkrhtsspirxrLsvALllklrkxffsRIgplflslsfSpalissskhhexkekgnQEk
                         |  ||          ||         |                 ||
OTSA  401  livnpydrdevaaaLdrAL    tmslaeRI         SrhaemldvivkndinhwQE RF1   672  kaiiyptfffIVavhtaxrrywlhkqltl
                     ||
OTSA  448    cfisdlkqIVprsaesqqrdkvatfpk
```

FIGURE 2A-2

```
RF3     1 rhgqtalrfxdtciivsmyixreikaytrgwxrlinlvvlscqlsfcqfpsxtstqlskqq

OTSA    1                                                           mtm

RF3    62 SRLtnxvltyrliktxnydygxrxgatdlVfrgxhycgvqqASrdnhxktavrdstsdams
          |||                          |           ||
OTSA    4 SRL                        vvVsnriappdehaASagglavgilgalkaaggl RF3   123 sgGWSrrwkgxrrrtlsvvrmawardsxrxegsgeeglaGkvxcrthlperxnrDlhYNgF
            |||                                  |              |  || |
OTSA   41 wfGWS                   getgnedqplkkvkkGnitwasfnlseqdlDeyYNqF RF3   184 SNsiLWPlFHYhpgeinFdenAWfgxrxgatpdvhqrdcxdyepxrfnlgaxlpfdvgsgn
          ||  ||| |||      |   ||
OTSA   83 SNavLWPaFHYrldlvqFqrpAW dgylrvnalladkllpllqdddiiwihdyhllpfahe RF3   245 vesqdsreatakrxgrvvPahtIpfexnlqnltcqtrdfegcfelxfsrvphirLcktflv
                            |   |                               |
OTSA  143 lrkrgvnnrigfflhipfPtpeIfnalptydtlleqlcdydllgfqtendrlafLdclsnl RF3   306 fRaksaxrehiaxWGgiqgrfvnvgafPIGIdvdKftdglkkesvqkriqQLKetfKgcki
           |           ||            ||||   |               |||   |
OTSA  204 tRvttrsakshtaWG    kafrtevyPIGI epKeiakqaagplppklaQLKaelKnvqn
```

FIGURE 2B-1

```
RF3   367 IvgVdRLDYiKGvPsevarhgsvsErasrmeGqgcsgtgcsakswrcgrvpifkicgqxvg
          |  | |||| || |          |       |
OTSA  260 IfsVeRLDYsKGlPerflayeallEkypqhhGkirytqiaptsrgdvqayqdirhqlenea

*
RF3   428 rxnhGqfGtvefvPihfmhksipfeeLislyavSDVcLVsstRDGMNLVsyEY iAcqeek
              |  |     |            |      ||| ||   |||||||  ||  |
OTSA  321 grinGkyGqlgwtPlyylnqhfdrklLmkifrySDVgLVtplRDGMNLVakEYvaAqdpan RF3   488 kGsLiLSeFtGAAqsLngAiIVNPwntDdlsdAineALTlpdvkkevnwekLykyISkyts
           | | || | |||  |  | ||||   |    |   |||            |   ||
OTSA  382 pGvLvLSqFaGAAneLtsAlIVNPydrDevaaAldrALT          msLaerIS

*
RF3   549 afwgenfvhelystssstsssatknxxtrckmrrssipgpvfsalssihffyyfixnyiN
                                                                     |
OTSA  429                                                  rhaemldvivkN RF3   610 DItetphvlsysltpvcsavteaaqvvfftyrpsfslsfflsraDLffetsxikrkrksrk
          ||                                          ||
OTSA  441 DI                                 nhwqecfisDL RF3   671 kshnlshiffycrcshritkilATxtidi
                                ||
OTSA  454       kqivprsaesqqrdkvATfpk
```

FIGURE 2B-2

METHODS AND COMPOSITIONS RELATED TO THE PRODUCTION OF TREHALOSE

This is a continuation, of application Ser. No. 07/893,099, filed May 27, 1992, now abandoned.

INTRODUCTION

1. Field of the Invention

This invention relates to DNA sequences which encode for genes in the trehalose biosynthetic pathway.

2. Background of the Invention

Sugars are commonly used to preserve and stabilize a variety of organic materials including foodstuffs, pharmaceuticals, cosmetics, etc. One disaccharide, trehalose (α-D-glucopyranosyl-α-D-glucopyranoside), found in large amounts in several organisms capable of surviving complete dehydration is an especially attractive additive for the long-term preservation of various biomolecules.

For example, U.S. Pat. No. 4,857,319 discloses an improved method for preserving liposomes, useful in the encapsulation of drugs and other therapeutic agents, in which trehalose is the particularly preferred dissacharide preserving agent. U.S. Pat. No. 4,806,343 describes a method of freezing artificial red blood cells in the presence of trehalose as the cryoprotectant. U.S. Pat. No. 4,891,319 is directed to a method of protecting proteins and other biological molecules against denaturation during drying by providing a certain percentage of trehalose to the system. U.S. Pat. No. 5,026,566 describes the incorporation of trehalose into pulverized food material before drying to retain freshness of the food product when re-hydrated.

Composed of two glucose molecules, trehalose is a highly symmetrical molecule. There are no direct internal hydrogen bonds, which may permit the molecule more flexibility than other disaccharides. It will not caramelize except under extreme heat, it is bland, non-toxic to humans, and has an even lower disaccharide bond energy (less than −1 kcal/mol) than sucrose (>27 kcal/mol). Although sucrose is also a non-reducing sugar, sucrose's higher bond energy renders it reactive with biological macromolecules such as the amino groups of proteins whereas trehalose is not reactive with such chemical groups.

Trehalose is found in various organisms. In particular, it has been observed that trehalose is often present in significant amounts (up to 20% dry weight) in organisms known as "anhydrobiotic" or "cryptobiotic" which have the ability to survive complete dehydration. Some examples of such organisms include Streptomyces sp. spores, dry active bakers yeast, brine shrimp cysts, some nematode species (adult and larvae), a pre-pupal larvae of the sawfly *Trichiocampus populi* Okamoto, and at least one plant species, the resurrection plant *Selaginella lepidophylla*.

Trehalose is not only associated with cryptobiogenic organisms. The presence of trehalose in some anhydrobiotic and some non-anhydrobiotic organisms correlates with the ability to positively respond to one or more stresses such as osomotic stress, frost, dehydration, chemical toxins, etc. For example, yeast respond to desiccation stress and to heat shock by the production of trehalose suggesting that trehalose serves a protective function (Hottiger et al., *FEBS Letters*, (1987) 220:113–115). The same correlation has been reported with respect to trehalose accumulation in yeast and freeze tolerance (Hino, et al., *App. & Environ. Microbiol.* (1990) 56:1386–1391) or exposure to hazardous chemicals (Attfield, P. V., *FEBS Lett.* (1987) 225:259–263).

Likewise, in *E. coli*, correlations between intracellular accumulation of trehalose and the osmotic strength of the growth medium have been noted (Strom et al., *FEMS Microbiol. Rev.* (1986) 39:79–86). It is also seen that mutants (ots) of *E. coli* which are defective in trehalose synthesis display reduced osmotic tolerance (Giaever, et al., *J. Bacteriol* (1988) 170:2841–1849) and reduced stationary phase induced heat tolerance (Hengge-Aronis, et al., *J. Bacteriol.* (1991) 178:7911–7917).

In both yeast and *E. coli*, trehalose is produced as a result of the action of two enzymes, a trehalose-6-phosphate synthase (trehalose synthase) and a trehalose-6-phosphate phosphatase (trehalose phosphatase). The trehalose synthase converts a UDP-glucose and a glucose-6-phosphate to trehalose-6-phosphate which is then acted upon by the trehalose phosphatase to result in trehalose.

Currently, production of trehalose involves extraction from yeast cells, resulting in high costs. It would be desirable to have access to genes which encode the trehalose synthase enzyme and/or the trehalose phosphatase enzyme to produce such enzymes in a controlled manner in a host cell of choice for in vitro applications. In addition, access to such genes could provide for expression of trehalose in a controlled manner in a host cell of choice.

Relevant Literature

Scripture, et al., *J. Mol. Biol.* (1987) 197:37–46 provides DNA sequence of three open reading frames designated as the "high affinity" L-arabinose transport operon located at 45 minutes on the *E. coli* chromosome. The third open reading frame, araH, is described as extending for 987 nucleotides.

Giaever, et al., *J. Bacteriol.* (1988) 170:2841–2849 reports the partial characterization of an *E. coli* trehalose-6-phosphate synthase through analysis of osmoregulatory trehalose synthesis (ots) insertion mutants.

Rod, et al., *J. Bacteriol.* (1988) 170:3601–3610 reports that the original *E. coli* K-12 carries an amber mutation in a gene involved in trehalose production. Osmotolerant functioning was restored by insertion of any one of three identified amber suppressor mutations.

Nelson, et al., *J. Biol. Chem.* (1989) 264:1775–1778 provides a yeast DNA sequence with four open reading frames. The second reading frame shows about 80% sequence with subunit B of Arabidopsis vacuolar $H^+$-ATPase.

Londesborough and Vuorio, *J. Gen. Microbiol.* (1991) 173:323–330, report the purification of a yeast protein complex having trehalose-6-phosphate phosphatase and a modified trehalose-6-phosphate synthase activity containing three major polypeptides.

Styrvold, O. B. and Strom, A. R., et al,. *J. Bacteriol.* (1991) 173:1187–1192 reports that the amber mutations of Rod, et al., supra, are not found in the otsA or otsB genes of Giaever, et al., supra. The authors note that the amber mutation may be in a gene which regulates the transcription of ots genes.

Klein, et al., *Res. Microbiol.* (1991) 142:359–371, mailed to subscribers on May 27, 1991, states that Arne Strom and co-workers, the co-inventors herein, advised that otsb is found adjacent to otsA on the same operon and that otsb encodes the trehalose-6-phosphate phosphatase.

Kaasen, et al., *J. Bacteriol.* (1992) 174:889–898, provide evidence that otsBA is an operon encoding trehalose-6-phosphate phosphatase and trehalose-6-phosphate synthase and the location of these genes. This paper is specifically incorporated by reference in its entirety.

BRIEF DESCRIPTION OF THE FIGURES

FIGS. 1A–I—Preliminary DNA sequence of an approximately 2.9 kb HindIII fragment (pFF106) of the 41- to 42-minute region fo the *E. coli* chromosome is shown (SEQ ID NO:1). The sequence from nucleotides 970–1259 has only been determined in one orientation. The first 505 bp of the DNA sequence and the translated amino acid sequence (SEQ ID NO:2) correspond to the 3' end of the adjacent araH gene (Scripture, et al., supra).

The otsB encoding region is presumed to begin at the GTG codon at position 675–677. The open reading frame which contains this otsB region extends from nucleotides 468–1472. An ATG codon is also noted in this open reading frame at position 618. The stop codon for the otsB gene has not been conclusively identified. The translated amino acid sequence of otsB (SEQ ID NO:3) from the presumed GTG start codon through the end of the open reading frame (675–1472) is shown directly below the corresponding encoding sequence.

The otsA encoding region is presumed to begin at one of the ATG codons at positions 1444–1446 and 1450–1453. The open reading frame which contains this otsA region extends from nucleotides 1405 to 2868. No translation stop codon has been discovered in the sequenced HindIII fragment, and the otsA encoding region may extend past the HindIII site at the end of the sequenced fragment. The translated amino acid sequence of otsA (SEQ ID NO:4) from the ATG codon at position 1444–1446 through the end of the sequenced fragment (1444–2868) is shown directly below the corresponding encoding sequence.

FIGS. 2A-1,2 and 2B-1,2 Regions of homology detected between the deduced *E. coli* otsA amino acid sequence (SEQ ID NO:4) and the translated amino acid sequences of the DNA region downstream of the yeast ATPase gene (Nelson, et al., supra) are shown in this figure. Yeast sequence, RF1 (SEQ ID NO:5) and RF2 (SEQ ID NO:6), is shown in the top line, *E. coli* sequence is shown on the bottom. Amino acids are represented by their one letter codes, with "X" representing stop codons. A line between the two sequences indicates identical amino acids. FIGS. 2A-1,2 shows the amino acid sequence comparison of the otsA encoded sequence to the translated amino acid sequence of the Nelson, et al., yeast sequence from nucleotides 2960 to 5059. The location of "ORF3" is indicated by the asterisks over the initial Met and C-terminal Thr amino acids. FIG. 2B-1,2 shows the amino acid sequence comparison in a different reading frame from. The location of "ORF4" is indicated by the asterisks over the initial Met and the C-terminal Asn amino acids.

SUMMARY OF THE INVENTION

This invention relates to genes involved in the biosynthesis of trehalose, trehalose-6-phosphate synthase (trehalose synthase) and trehalose-6-phosphate phosphatase (trehalose phosphatase). Recombinant constructs, including chimeric genes adapted for expression of a trehalose biosynthetic enzyme in a plant cell, and host cells (prokaryotic and eukaryotic) containing such constructs are provided. Methods for producing trehalose biosynthetic enzymes in a host cell are described. Methods to produce trehalose in a host cell by the expression of a DNA sequence encoding a trehalose synthase and a DNA sequence encoding a trehalose phosphatase are also provided. Host cells containing recombinant DNA constructs encoding for a trehalose synthase, trehalose phosphatase or both trehalose synthase and trehalose phosphatase are described. Host cells containing increased amounts of trehalose biosynthetic enzyme(s) and/or trehalose, as compared with wild type levels of trehalose are also enabled. The production, or overproduction, of trehalose in a host cell may impart one or more of the osmotic, freeze, frost chemical tolerance or protein and/or lipid protective attributes of trehalose to such cell.

DETAILED DESCRIPTION OF THE INVENTION

As noted above, a synthase and a phosphatase, respectively, catalyze the final two steps in the production of trehalose. Trehalose synthase acts upon UDP-glucose and glucose-6-phosphate, substrates typically found in abundance in eukaryotic and prokaryotic cytoplasm, to form trehalose-6-phosphate. The trehalose-6-phosphate is then acted upon by the trehalose phosphatase to yield trehalose.

For purposes of this invention, a trehalose biosynthetic enzyme includes any sequence of amino acids, peptide, polypeptide or protein whether derived in whole or in part from natural or synthetic sources which demonstrates the above-described synthase and/or phosphatase activity. Typically, a DNA sequence encoding a trehalose biosynthetic enzyme will be derived in whole or in part from a natural gene. However, DNA sequences encoding modified trehalose biosynthesis enzymes, such as DNA sequences encoding mutated or truncated enzymes, fusion proteins resulting from the expression of a single DNA sequence encoding both a trehalose synthase and trehalose phosphatase activity, sequences modified to utilize plant-preferred codons, and the like are also contemplated hereunder. By enzyme reactive conditions is meant that any necessary conditions available in an environment (i.e., factors such as temperature, pH, lack of inhibiting substances) which will permit the enzyme to function.

DNA sequences encoding an *E. coli* trehalose synthase and an *E. coli* trehalose phosphatase and recombinant constructs having such sequences are provided hereunder. The DNA sequence of pFF106 (ots$^+$ otsB$^+$), a HindIII fragment containing sequence from the otsBA operon is provided in FIG. 1. A yeast trehalose synthase sequence (Nelson,et al., supra) is also identified herein. The activities of the encoded trehalose biosynthetic enzymes are representative of the properties and characteristics contemplated herein. From the exemplified *E. coli* and yeast trehalose biosynthetic enzymes and sequences, related trehalose biosynthetic sequences are readily obtained and tested. The respective trehalose synthase and/or trehalose phosphatase activity encoded by a given DNA sequence of interest may be determined upon expression of such sequence or sequences in a host cell. One may assay for activity of trehalose synthase or trehalose phophatase directly or, alternatively, the production (or increased production in cells which normally produce trehalose) of trehalose in a host cell may be used to deduce the activity of a peptide encoded by such DNA sequence. The presence of trehalose may be readily determined through the use of gas chromatography and other methods.

One skilled in the art will be able to identify various trehalose mutants useful or required to such testing. For example, the use of a *E. coli* K-12 strain which does not carry an amber mutation that causes decreased accumulation of trehalose is osmotically stressed cells is desired. This mutation has been mapped to the katF region of *E. coli*. Thus, MC4100 (CGSC 6152) derivatives are otsX$^+$ whereas N1485 (CGSC 5024) derivatives are otsX$^-$ (Kaasen, supra). Furthermore, methods to obtain strains deficient in otsA are described in Styrovold and Strom, supra. Methods to obtain strains deficient in otsB or otsA and otsB are described in Kaasen, supra. One mutant, *E. coli* FF4050 containing plasmid pFF106 is on deposit at the American Type Culture Collection, Rockville, Md., accession number ATCC 69002. The FF4050 strain (MC4100 Δ[otsA1::Tn0Φ(otsB-lacZ)8]1 Δ(treA::Tn10) recA56 Sr1-300::Tn10 otsX⁺ MC4100) cured of the pFF106 plasmid will lack trehalose synthase and trehalose phosphatase activity.

One skilled in the art will readily recognize that antibody preparations, nucleic acid probes (DNA and RNA) and the like may be prepared and used to screen and recover "homologous" or "related" trehalose biosynthetic enzymes from a variety of sources. Typically, nucleic acid probes are labeled to allow detection, preferably with radioactivity although enzymes or other methods may also be used. For immunological screening methods, antibody preparations either monoclonal or polyclonal are utilized. Polyclonal antibodies, although less specific, typically are more useful in gene isolation. For detection, the antibody is labeled using radioactivity or any one of a variety of second antibody/ enzyme conjugate systems that are commercially available. Examples of some of the available antibody detection systems are described by Oberfilder (*Focus* (1989) BRL Life Technologies, Inc. 11:1–5).

Homologous sequences are found when there is an identity of sequence, which may be determined upon comparison of sequence information, nucleic acid or amino acid, or through hybridization reactions between a known trehalose biosynthetic enzyme and a candidate source. Conservative changes, such as Glu/Asp, Val/Ile, Ser/Thr, Arg/Lys and Gln/Asn may also be considered in determining sequence homology. Typically, a lengthy nucleic acid sequence may show as little as 50–60% sequence identity, and more preferably at least about 70% sequence identity, between the target sequence and the given plant thioesterase of interest excluding any deletions which may be present, and still be considered related. Amino acid sequences are considered homologous by as little as 25% sequence identity between the two complete mature proteins. (See generally, Doolittle, R. F. OF URFS and ORFS (University Science Books, CA, 1986).

A genomic or other appropriate library prepared from the candidate endogenous trehalose containing organism of interest may be probed with conserved sequences (See, FIGS. 2A & 2B) from the trehalose biosynthetic enzyme to identify homologously related sequences. In a preferred embodiment, a trehalose biosynthetic enzyme of this invention will have at least about 30% sequence identity, and more preferably at least about 50% sequence identity with at least a sequence of 8 amino acids of an exemplified trehalose biosynthetic enzyme sequence or trehalose biosynthetic enzyme which has in turn been obtained from a different source. Alternatively, a biosynthetic enzyme of this invention will have at least about 65% sequence identity and more preferably at least about 75% sequence homology with an exemplified trehalose biosynthetic enzyme or a trehalose biosynthetic enzyme which in turn has been obtained from a given trehalose biosynthetic sequence.

The expression of a DNA sequence encoding a trehalose synthase and/or trehalose phosphatase may be obtained in a host cell of interest. In a like manner, trehalose itself may be caused to be produced in any host cell for which UDP-glucose and glucose-6-phosphate substrates are available by ensuring that a trehalose-6-phosphate producing enzyme and dephosphorylating enzyme are provided. Host cells of interest for the production of trehalose or expression of trehalose synthase or trehalose phosphatase include prokaryotes and eukaroytes. Increased production of trehalose in organisms already capable of producing trehalose, e.g., *E. coli* and *S. cerevisiae*, by over-expression of trehalose synthase and/or trehalose phosphatase, is likewise contemplated hereunder. In at least one trehalase defective mutant (treA), LCB107 (CGSC 6407), osmotically stressed *E. coli* over-produced trehalose which was then excreted by the cell and accumulated in the growth medium (Styrvold and Strom, supra). Choice of methods to introduce the DNA sequence (s) encoding the trehalose biosynthetic genes, selection markers, vectors, etc., will depend upon the host cell.

Intracelluar accumulations of trehalose-6-phosphate are toxic to *E. coli*, (Kaasen, et al., supra) and therefore, it is noted that it may be toxic to other cells. Thus, in instances in which production of trehalose synthase itself is desired, it may be required to target the enzyme for extraceullar deposition or to cell compartments which do not contain the UDP-glucose or glucose-6-phosphate substrates. When trehalose production in a host cell is desired, it may be necessary to ensure at least an equivalent level of phosphatase activity to avoid trehalose-6-phosphate buildup. A variety of means may be employed to provide adequate trehalose phosphatase activity as compared with trehalose synthase activity, including but not limited to the choice of respective transcription initiation regions (promoters) employed to direct the expression of the respective trehalose synthase and trehalose phosphatase sequences (i.e., strength and specificity may be significantly altered) or gene fusion whereby the production of a single trehalose biosynthetic enzyme having synthase and phosphatase activity is produced, and the like. From the observed activity of the pFF106 fragment (Kaasen, supra) which is considered to contain a partial trehalose synthase sequence, the design of such a fusion protein may be suggested.

Preferably, for the production of trehalose, the use of a trehalase deficient host cell to prevent the in vivo degradation of trehalose is desired. Trehalase deficient cells may be obtained through selection of mutants (native or mutagenized) or genetic engineering (e.g., anti-sense, ribozymes, co-suppression, etc. of the trehalase gene). Trehalose producing organisms are typically capable of producing trehalase. (See, Gutierrez, et al., *Mol. Gen. Genet.* (1989) 217:347–354, which provides DNA sequence of periplastric trehalase of *E. coli* K12.) But trehalase is found in many organisms, including organisms which do not produce trehalose as well. (See, Ruf, et al., *J. Mol. Biol.* (1990) 265:15034–1039, which provides DNA sequence of rabbit small intestinal trehalase.).

As mentioned above, choice of a given transcription initiation region will depend upon the intended use. For some applications, it may be useful or necessary to control the production of trehalose by the use of tissue/timing specific promoters controlling the transcription and translation of the inserted trehalose biosynthetic gene(s). For example, if the production of trehalose affects the viability of a host cell by the re-direction of UDP-glucose or glucose-6-phosphate into trehalose instead of other cell functions, one may be able to mitigate such effects by directing expression of the trehalose biosynthetic gene(s) at particular growth stages, or in multicellular organisms, into particular types of tissues, particularly carbohydrate storage organs or tissues. In the event that the required substrate(s) are localized in a discrete cellular organelle one may choose to employ an associated target peptide with or without tissue/ timing specific promoters.

As stated earlier, by this invention, one may seek to produce the trehalose biosynthetic enzymes in a host cell to be harvested and used to produce trehalose in vitro. Alternatively, it may be desired to produce trehalose within the host cell itself. Trehalose produced in a cell may, in part, be excreted into the surroundings (culture medium). The production or over-production of trehalose in a host cell may impart one or more of osmotic, freeze, frost, chilling, or chemical tolerance or protein and/or lipid protective phenotypes associated with the presence of trehalose in other organisms to such cell.

Plants, especially higher plants (spermatophytina), are of particular interest for the production of trehalose not only as a source for trehalose or with respect to useful stress-related properties that expression of trehalose may impart to the cell, but as a means to impart improved characteristics to plant products by the in planta presence of trehalose. Some examples of plants which may be useful hereunder include carbohydrate storage plants (such as sugar cane, sugar beet, potato, etc.), fruits and vegetables which are normally subjected to significant processing (such as tomatoes, strawberries, applies, etc.) any commercially important crop which finds possible exposure to trehalose correlated stress (cotton, corn, rapeseed, alfalfa, etc.) and crops of horticultural interest (carnations, petunias, orchids, etc.). A plant host cell of interest may be found in any form, including but not limited to protoplasts, callus, cuttings, or whole plants.

When trehalose or the expression of an enzyme in the trehalose biosynthetic pathway is desired in a whole plant, a means to insert the gene of interest into the plant cell genome and recover a transgenic plant is needed. The method of transformation is not critical to the instant invention; various methods of plant transformation are currently available. As newer methods are available to transform crops, they may be directly applied hereunder. For example, many plant species naturally susceptible to Agrobacterium infection may be successfully transformed via tripartite or binary vector methods of Agrobacterium mediated transformation. In addition, techniques of microinjection, DNA particle bombardment, direct DNA uptake, chemically mediated transformation, electroporation, and the like, have been developed which allow for the transformation of various monocot and dicot plant species. When expression in a plant cell is desired, it may be desirable to modify the DNA sequence(s) encoding the trehalose biosynthetic enzyme to more closely follow sequences typically found in plant cells (See, WO 90/10076). Moreover, the use of eukaryotic sequences (i.e., yeast) may be preferred over the use of prokaryotic sequences (i.e. E. coli) for use in plants as well.

The following examples are provided by way of illustration and not by way of limitation.

EXAMPLES

Example 1
Trehalose-6-Phosphate Synthase Assay

Trehalose synthase activity may be detected by this method in *E. coli* strains which are defective in the synthesis of the periplasmic trehalase; i.e., carry a treA mutation. In strains which produce trehalase, the synthase activity will be masked by the trehalase activity. A chromosomal treA mutation can be inserted by infecting the strain for testing with a P1 lysate prepared from a strain which carry a treA::Tn10 insertion such as UE5 (Boos, et al., *J. Biol. Chem.* (1987) 262:13212–13218) or its decedent FF4171 (Styrvold and Strom, supra).

To increase the synthase activity, the cells for testing may be grown aerobically at 37° C. in a medium of elevated osmotic strength; e.g., medium 63-glucose (Miller, J. H. (1972) *Experiments In Molecular Genetics*, Cold Spring Harbor Laboratory, Cold Spring Harbor, N.Y.) with 0.4M NaCl added. As a pre-treatment, harvested cells for testing are washed once in 10 mM sodium phosphate (pH 7.5) by centrifugation. (If necessary for practical reasons, they may be stored at −80° C.). To permeabilize the cells, 10% (vol/vol) toluene is added to 3 to 5 ml of ice-cold cell suspension containing 100 to 200 mg of cell protein. The mixture is vortexed for 1 min; 6 ml of 0 mM Tris hydrochloride (pH 7.5) is then added and the mixture centrifuged at 6,000×g for 5 min. (4° C.). The cells are washed twice by centrifugation in 10 ml of Tris buffer and then suspended at a protein concentration of 20 mg/ml in Tris buffer containing 2 mM dithiothreitol. The cells are now ready for the assay.

A standard reaction mixture for determination of trehalose-6-phosphate synthase activity contains (in a 0.3 ml volume) 2.75 $\mu$mol of UDP-glucose (Sigma Chemical Co., St. Louis, Mo.), 4.5 $\mu$mol of glucose 6-phosphate (Sigma), 0.75 $\mu$mol of $MgCl_2$, 10 $\mu$mol of Tris hydrochloride (pH 7.5), 75 $\mu$mol of KC1, and 1 mg of cell protein. The reaction mixture is incubated at 37° C. for various times up to 6 min., and then the reaction is terminated by heating for 5 min. in a boiling water bath. Sucrose (0.3 $\mu$mol in a 30 $\mu$l volume) is then added as an internal standard, and denatured protein removed by centrifugation. A sample of 280 $\mu$l is withdrawn, the pH adjusted to 8.0 with 2.5 $\mu$mol of Tris base, and 1U of alkaline phosphatase (Sigma) added. After incubation at 37° C. for 2 hr., the reaction is stopped by heating. For desalting, a sample of 250$\mu$l is applied to a column (0.5 by 2 to 6 cm) packed with equal amounts of Dowex 50X4-200 in $H^+$ form and Dowex 1X8-400 in formate form. Free sugars are washed through the column with 1 to 3 ml of water, and the eluate freeze-dried. Gas chromatography is preformed as described in Example 3B. The enzyme unit is nanomoles of trehalose formed per minute at 37° C.

Example 2
Trehalose-6-Phosphate Phosphatase Assay

The phosphatase activity may be determined in *E. coli* which carry a treA mutation. The treA mutation can be introduced in the strain for testing and harvested cells may be prepared for the assay as described in the pretreatment steps outlined in Example 1.

A standard reaction mixture for determination of phosphatase activity contains (in a 150 $\mu$ volume) the following: 1.5 $\mu$mol of trehalose-6-phosphate (Sigma), 5 $\mu$mol of Tris-hydrochloride (pH 7.4), 0.4 $\mu$mol of $MgCl_2$, and 125 to 500 $\mu$g of cell protein. The reaction mixture is incubated up to 12 min. at 37° C., and the reaction is terminated by heating for 5 min. in a boiling-water bath. Sucrose (0.25 $\mu$mol in a 25 $\mu$l volume) is then added as an internal standard, and denatured protein removed by centrifugation. For desalting, a sample of 150 $\mu$l is applied to a column (0.5 by 2 cm) packed with equal amounts of Dowex 50X4-200 in $H^+$ form and Dowex 1X8-400 in formate form. Free sugars are washed through the column with 1 ml of water, and the eluate may be freeze-dried. Gas chromatographic determination of trimethylsilylated trehalose may then be applied as described in Example 3B. One unit of trehalose phosphatase activity equals 1 nmol of trehalose produced per min. at 37° C.

Example 3
Trehalose Detection

A. The cells are washed by centrifugation in medium 63 (Miller, supra) without sugar and containing an appropriate amount of NaCl. The cells are extracted with 0.4M perchloric acid to inactivate trehalase, if present, and to liberate trehalose. The extract is then neutralized with KOH and precipitated potassium perchlorate is removed. Trehalose in the extract may be determined by the anthrone method after the reducing sugars are destroyed by boiling with alkali as described in the literature (Lapp, 1971; Larsen, 1987). The results may be verified by gas chromatographic analysis as follows.

B. An HP5890A gas chromatograph, equipped with an HP3393A integrator, and an HP1 capillary column (25 m by 0.31 mm [inner diameter]; Hewlett-Packard Co., Avondale, Pa.) may be used. Helium is used as the carrier gas. The injector and detector temperatures are 250 and 300° C., respectively. The column temperature is kept at 190° C. for 2 min. followed by a temperature increase of 30° C. per min. to 250° C., after which the temperature is kept at 205° C. for 10 min. The freeze-dried trehalose samples are dissolved in a proper amount (e.g. 20 µl) of dimethylformamide and then trimethylsilylated by the addition of a proper amount (e.g. 20 µl) of bis(trimethylsilyl)-trifluoroacetamide containing 1% trimethylchlorosilane. Sucrose may be used as an internal standard.

Example 4
Production of Osmotrically Sensitive Mutants

A culture carrying a random selection of lacZ operon fusions may be prepared by infecting *E. coli* strain MC4100 (CGSG 6152) with the phage λ placMu55 (Km$^r$) and the helper phage λ pMu507 (Bremer, et al., *J. Bacteriol* (1985) 162:1092–1099; May, et al., Mol. Gen. Genet. (1986) 205:225–233). The infected cells are plated on 100 plates with LB medium and 60 µg of kanamycin per ml, about 50,000 Km$^r$ colonies may then be collected. This collection of Km$^r$ mutants is grown in medium 63-glucose and then inoculated into the same medium with 0.45M NaCl added. The latter culture is incubated for 2 hr. at 37° C. before 100 µg of ampicillin per ml is added and then incubation is continued for 5 hr. The surviving Km$^r$ cells are grown in LB medium overnight, and the whole ampicillin enrichment procedure repeated once before the cells are plated on medium 63-lactose-0.2M NaCl-agar.

Osmotically sensitive mutants are then isolated by transferring an inoculant of the individual colonies to two sets of agar plates, one containing medium 63-glucose and one containing the same medium with 0.5M NaCl. Osmotically sensitive mutants can be further characterized by assaying for trehalose accumulation as described in Example 3 and using the respective trehalose synthase (otsA) and trehalose phosphatase (otsB) assays in Example 1 and Example 2, respectively.

Example 5
Production of Trehalose

Plasmid pFF106 (FIG. 1) was introduced into strain FF4037 (Kaasen, 1992) using standard techniques. In FF4037 (MC4100 Δ[otsA1::Tn10Φ(otsB-lacZ)8]1 treA::Tn10 otsX$^+$ $_{MC}$4100), the otsBA genes are deleted from the chromosome and the strain carries a chromosomal treA mutation to prevent synthesis of the periplasmic trehalase. Cells of FF4037(pFF106) were grown aerobically at 37° C. in medium 63-glucose with 0.4M NaCl added. The glucose concentration was 22 mM at start. The cells were grown until the optical density of the culture measured 7 at 420 nm. The cells were then collected by centrifugation and resuspended in the same volume of a medium which was identical to the growth medium except that ammonium sulfate was replaced with potassium sulfate. In other words, to prevent bacterial growth the new medium did not contain any nitrogen source. The resting cells of FF4037(pFF106) were incubated aerobically at 37° C. in the new medium for 20 hrs.

At intervals, bacterial cells in 1 ml volume of culture were removed by centrifugation. Sucrose (1 µmol in a 200 µl volume) was added as an internal standard to 801 µl of supernatant. For desalting, a sample of 200 µl was then applied to a column (0.5 by 2 cm) packed with equal amounts of Dowex 50X4-200 in H+ form and Dowex 1X8 in formate form. Free sugars were washed through the the column and 1 ml of water, and the eluate was freeze-dried and analyzed for trehalose and glucose by gaschromatography as described in Example 3.

The analyses showed that during the incubation period the glucose content of the medium decreased and the trehalose content increased (Table 1). After 20 hrs. incubation, 18 µmol glucose had disappeared per ml of medium and 2.2 µmol of trehalose were produced per ml of medium. In other words, trehalose produced by the resting cells of FF4037 (pFF106) was excreted into medium. Since the production of one molecule of trehalose requires two glucose molecules, up to 24% of glucose converted could be found in trehalose produced (Table 1).

TABLE 1

Conversion of Glucose and Production of Trehalose by Resting Cells of *E. coli* Strain FF4037 (pFF106)

| Incubation Time (h) | Glucose Converted (µmol per ml) | Trehalose Produced (µmol per ml) | Yield (%) |
|---|---|---|---|
| 1 | 2.4 | 0.2 | 17 |
| 4 | 8.0 | 0.6 | 15 |
| 8 | 12.0 | 1.2 | 20 |
| 20 | 18.0 | 2.2 | 24 |

Example 6
Comparison of Yeast and *E. coli* Sequence

A computer aided search of sequence data bases using the deduced amino acid sequence of the otsA protein (FIG. 1) was conducted. Regions of homology were detected between the deduced otsA amino acid sequence and the translated amino acid sequences of the open reading frames, ORF3 and ORF4, located downstream of the yeast ATPase gene (Nelson et al., supra). Homology with otsA was found in the translated ORF3 and ORF4 amino acid sequences, as well as in the translated amino acid sequence of the intervening DNA region which was represented by Nelsen, et al. as non-coding sequence. Furthermore, homology to otsA was apparent in the translated amino acid sequences from at least two reading frames of the yeast sequence (FIGS. 2A & 2B). Thus, the published yeast DNA sequence must contain several errors which cause false stop signals and/or frame shifts in the sequenced reading frames.

Example 7
Expression of Yeast Sequence in *E. coli*

A YEp13 derived plasmid carrying a yeast ATPase gene and its downstream region (Nelson,et al., supra) was introduced into an otsA mutant, FF4052 using standard infection procedure and selecting for ampicillin resistant colonies. Strain FF4052 is a recA mutant of FF4026 (Kaasen, et al., supra), and it is constructed by transducing FF4026 with a P1 lysate prepared from a recA-containing strain, FF1005 (Kaasen, et al, supra). FF4052 carrying the plasmid grew on agar plates with medium 63-glucose-0.5M NaCl, whereas the parental plasmid free strain did not grow. Trehalose accumulation in osmotically (0.4M NaCl) stressed cells of FF4052 carrying plasmid YEp13-ATPase, was confirmed by gaschromatographic analysis as described in Example 3. The restoration of the osmotic tolerant phenotype and trehalose accumulation indicates that the yeast DNA encodes a functional trehalose synthase.

Additionally, a 2.1 kb NarI fragment of the YEp13-ATpase plasmid, which encompasses the yeast DNA inferred to code a trehalose synthase, was subcloned into the ClaI site of pGEM-7Zf(−) (Promega Corp., Madison, Wis.) using standard cloning procedures. This NarI fragment extends from base 2916 to the end of the yeast DNA at base 5059 (Nelson, et al., 1989), and extends additionally 38 bases into the YEp13 vector (Broach et al., Gene (1979) 8:121–133). The ligation mixture for this construction was transformed into strain DH5αF (BRL) and clones containing an insert was identified by use of so-called α-complementation. DNA of insert-containing clones was first characterized as to restriction fragment size after EcoRI and BamHI digestion, thereby utilizing the EcoRI site at position 4273 of the yeast DNA. Clones containing the wanted yeast fragment were identified as having three restriction fragments of 3.0 kb (pGEM vector), 1.3 kb and 0.8 kb. Plasmid pFF469 was identified by EcoRI digestion which yielded two restriction fragments of 3.8 kb and 1.3 kb. This showed that ORF3 and ORF4 of the yeast DNA is in opposite orientation to the lac promoter and the lacZ gene of the pGEM vector.

Plasmid pFF469 was introduced into an otsA mutant, FF4052, using standard procedure and selecting for ampicillin resistant colonies. Trehalose accumulation is osmotically stressed (0.4M NaCl) cells of FF4052(pFF469) as tested by gas chromatography was restored.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A purified recombinant construct comprising a DNA sequence encoding a bacterial trehalose biosynthetic enzyme selected from the group consisting of trehalose synthase and trehalose phosphatase.

2. The construct of claim 1 wherein said DNA sequence encodes a trehalose biosynthetic enzyme encoded on plasmid pFF106.

3. The construct of claim 2, wherein said DNA sequence comprises the trehalose phosphatase encoding region at nucleotides 675–1472 of SEQ ID NO:1.

4. The construct of claim 2, wherein said DNA sequence comprises the trehalose synthase encoding region at nucleotides 1450–2868 of SEQ ID NO:1.

5. The construct of claim 1 wherein said trehalose biosynthetic enzyme is from *E. coli*.

6. The construct of claim 5, wherein said DNA sequence encodes trehalose phosphatase.

7. The construct of claim 6 wherein said DNA sequence encodes the trehalose phosphatase protein represented as SEQ ID NO:3.

8. The construct of claim 6, wherein said DNA sequence encodes trehalose synthase.

9. The construct of claim 8 wherein said DNA sequence encodes the trehalose synthase protein represented as SEQ ID NO:4.

10. A host cell comprising a recombinant construct of claim 1.

11. A chimeric gene comprising, in the 5' to 3' direction of transcription, the following genetic elements linked in operable combination:

(i) a transcription initiation region functional in a plant cell;

(ii) a translation initiation region functional in a plant cell;

(iii) a DNA sequence encoding a trehalose biosynthetic enzyme selected from the group consisting of bacterial trehalose synthase and bacterial trehalose phosphatase; and (iv) a translation termination region functional in a plant cell.

12. A plant cell comprising a chimeric gene according to claim 11, wherein said gene is expressed.

13. A method of producing an increased amount of a trehalose biosynthetic enzyme in a host cell as compared with a wild type host cell normally capable of producing said enzyme, said method comprising:

inserting a DNA sequence into a host cell, said sequence encoding a trehalose biosynthetic enzyme selected from the group consisting of bacterial trehalose synthase and bacterial trehalose phosphatase, operably linked to regulatory elements for directing the expression of said enzyme in said host cell; and growing said host cell under conditions to permit the expression of said enzyme.

14. The method of claim 13 wherein said cell is a plant cell.

15. A method of producing a host cell for increased trehalose production comprising the steps of:

inserting a first DNA sequence into said host cell, said sequence encoding a trehalose synthase operably linked to regulatory elements for directing the expression of said trehalose synthase in said host cell in the presence of UDP-glucose and glucose-6-phosphate, and a second DNA sequence encoding a trehalose phosphatase operably linked to regulatory elements for directing the expression of said trehalose phosphatase in said host cell wherein trehalose phosphatase encoded by said trehalose phosphatase encoding DNA sequence is available to the product of said trehalose synthase in the presence of said UDP-glucose and said glucose-6-phosphate; and growing said host cell under conditions to permit the expression of said synthase and said phosphatase whereby trehalose is produced.

16. A host cell produced according to the method of claim 15.

17. A method of producing trehalose biosynthetic enzyme in a host cell otherwise incapable of producing said enzyme, said method comprising:

inserting a DNA sequence into a host cell, said sequence encoding a trehalose biosynthetic enzyme selected from a group consisting of bacterial trehalose synthase and bacterial trehalose phosphatase, operably linked to regulatory elements for directing the expression of said enzyme in said host cell; and growing said host cell under conditions to permit the expression of said enzyme.

18. The method of claim 17 wherein said cell is a plant cell.

19. A host cell according to claim 16, wherein said host cell is a plant cell and wherein said trehalose synthase and said trehalose phosphatase are from a bacteria.

* * * * *

SEQUENCE LISTING (1) GENERAL INFORMATION:

(iii) NUMBER OF SEQUENCES:  6

(2) INFORMATION FOR SEQ ID NO: 1:

(i) SEQUENCE CHARACTERISTICS:
      (A) LENGTH:   2868 base pairs
      (B) TYPE:   nucleic acid
      (C) STRANDEDNESS:   double
      (D) TOPOLOGY:   linear (ii) MOLECULE TYPE:   genomic DNA (xi) SEQUENCE DESCRIPTION: SEQ ID NO: 1:

```
AAGCTTCTTT GCCCTTGGTT ACGCCAACTG GTTCGGTCTG CCTGCGCCAA TCTGGCTCAC      60

CGTCGCGTGT CTGATTATCT TTGGTTTGCT GCTGAATAAA ACCACCTTTG GTCGTAACAC     120

CCTGGCGATT GGCGGGAACG AAGAGGCCGC GCGTCTGGCG GGTGTACCGG TTGTTCGCAC     180

CAAAATTATT ATCTTTGTTC TCTCAGGCCT GGTATCAGCG ATAGCCGGAA TTATTCTGGC     240

TTCACGTATG ACCAGTGGGC AGCCAATGAC GTCGATTGGT TATGAGCTGA TTGTTATCTC     300

CGCCTGCGTT TTAGGTGGCG TTTCTCTGAA AGGTGGCATC GGAAAAATCT CATATGTGGT     360

GGCGGGTATC TTAATTTTAG GCACCGTGGA AAACGCCATG AACCTGCTTA ATATTTCTCC     420

TTTCGCGCAG TACGTGGTTC GCGGCTTAAT CCTGCTGGCA GCGGTGATCT TCGACCGTTA     480

CAAGCAAAAA GCGAAACGCA CTGTCTGATG CTTTTTTCTG CAACAATTTA GCGTTTTTTC     540

CCACCATAGC CAACCGCCAT AACGGTTGGC TGTTCTTCGT TGCAAATGGC GACCCCCGTC     600

ACACTGTCTA TACTTACATG TCTGTAAAGC GCGTTCTGCG CAACACAATA AGAAAAGAGA     660

AGGAGGAGAA CCGGGTGACA GAACCGTTAA CCGAAACCCC TGAACTATCC GCGAAATATG     720

CCTGGTTTTT TGATCTTGAT GGAACGCTGG CGGAAATCAA ACCGCATCCC GATCAGGTCG     780

TCGTGCCTGA CAATATTCTG CAAGGACTAC AGCTACTGGC AACCGCAAGT GATGGTGCAT     840

TGGCATTGAT ATCAGGGCGC TCAATGGTGG AGCTTGACGC ACTGGCAAAA CCTTATCGCT     900
```

```
TCCCGTTAGC GGGCGTGCAT GGGGCGGAGC GCCGTGACAT CAATGGTAAA ACACATATCG      960

TTCATCTGCC GGATGCGATT GCGCGTGATA TTAGCGTGCA ACTGCATACA GTCATCGCTC     1020

AGTATCCCGG CGCGGAGCTG GAGGCGAAAG GGATGGCTTT TGCGCTGCAT TATCGTCAGG     1080

CTCCGCAGCA TGAAGACGCA TTAATGACAT TAGCGCAACG TATTACTCAG ATCTGGCCAC     1140

AAATGGCGTT ACAGCAGGGA AAGTGTGTTG TCGAGATCAA ACCGAGAGGT ACCAGTAAAG     1200

GTGAGGCAAT TGCAGCTTTT ATGCAGGAAG CTCCCTTTAT CGGGCGAACG CCCGTATTTC     1260

TGGGCGATGA TTTAACCGAT GAATCTGGCT TCGCAGTCGT TAACCGACTG GCGGAATGT      1320

CAGTAAAAAT TGGCACAGGT GCAACTCAGG CATCATGGCG ACTGGCGGGT GTGCCGGATG     1380

TCTGGAGCTG GCTTGAAATG ATAACCACCG CATTACAACA AAAAGAGAA AATAACAGGA      1440

GTGATGACTA TGAGTCGTTT AGTCGTAGTA TCTAACCGGA TTGCACCACC AGACGAGCAC     1500

GCCGCCAGTG CCGGTGGCCT TGCCGTTGGC ATACTGGGGG CACTGAAAGC CGCAGGCGGA     1560

CTGTGGTTTG GCTGGAGTGG TGAAACAGGG AATGAGGATC AGCCGCTAAA AAAGGTGAAA     1620

AAAGGTAACA TTACGTGGGC CTCTTTTAAC CTCAGCGAAC AGGACCTTGA CGAATACTAC     1680

AACCAATTCT CCAATGCCGT TCTCTGGCCC GCTTTTCATT ATCGGCTCGA TCTGGTGCAA     1740

TTTCAGCGTC CTGCCTGGGA CGGCTATCTA CGCGTAAATG CGTTGCTGGC AGATAAATTA     1800

CTGCCGCTGT TGCAAGACGA TGACATTATC TGGATCCACG ATTATCACCT GTTGCCATTT     1860

GCGCATGAAT TACGCAAACG GGGAGTGAAT AATCGCATTG GTTTCTTTCT GCATATTCCT     1920

TTCCCGACAC CGGAAATCTT CAACGCGCTG CCGACATATG ACACCTTGCT TGAACAGCTT     1980

TGTGATTATG ATTTGCTGGG TTTCCAGACA GAAAACGATC GTCTGGCGTT CCTGGATTGT     2040

CTTTCTAACC TGACCCGCGT CACGACACGT AGCGCAAAAA GCCATACAGC CTGGGGCAAA     2100

GCATTTCGAA CAGAAGTCTA CCCGATCGGC ATTGAACCGA AAGAAATAGC CAAACAGGCT     2160

GCCGGGCCAC TGCCGCCAAA ACTGGCGCAA CTTAAAGCGG AACTGAAAAA CGTACAAAAT     2220

ATCTTTTCTG TCGAACGGCT GGATTATTCC AAAGGTTTGC CAGAGCGTTT TCTCGCCTAT     2280

GAAGCGTTGC TGGAAAAATA TCCGCAGCAT CATGGTAAAA TTCGTTATAC CCAGATTGCA     2340

CCAACGTCGC GTGGTGATGT GCAAGCCTAT CAGGATATTC GTCATCAGCT CGAAAATGAA     2400

GCTGGACGAA TTAATGGTAA ATACGGGCAA TTAGGCTGGA CGCCGCTTTA TTATTTGAAT     2460

CAGCATTTTG ACCGTAAATT ACTGATGAAA ATATTCCGCT ACTCTGACGT GGGCTTAGTG     2520

ACGCCACTGC GTGACGGGAT GAACCTGGTA GCAAAAGAGT ATGTTGCTGC TCAGGACCCA     2580

GCCAATCCGG GCGTTCTTGT TCTTTCGCAA TTTGCGGGAG CGGCAAACGA GTTAACGTCG     2640

GCGTTAATTG TTAACCCCTA CGATCGTGAC GAAGTTGCAG CTGCGCTGGA TCGTGCATTG     2700

ACTATGTCGC TGGCGGAACG TATTTCCCGT CATGCAGAAA TGCTGGACGT TATCGTGAAA     2760

AACGATATTA ACCACTGGCA GGAGTGCTTC ATTAGCGACC TAAAGCAGAT AGTTCCGCGA     2820

AGCGCGGAAA GCCAGCAGCG CGATAAAGTT GCTACCTTTC CAAAGCTT                 2868
```

(2) INFORMATION FOR SEQ ID NO: 2:

(i) SEQUENCE CHARACTERISTICS:
        (A) LENGTH:   168 amino acids
        (B) TYPE:     amino acid
        (D) TOPOLOGY: linear (ii) MOLECULE TYPE:   peptide (xi) SEQUENCE DESCRIPTION: SEQ ID NO: 2:

Ser Phe Phe Ala Leu Gly Tyr Ala Asn Trp Phe Gly Leu Pro Ala Pro

```
                 1               5                    10                   15
            Ile Trp Leu Thr Val Ala Cys Leu Ile Ile Phe Gly Leu Leu Leu Asn
                            20                  25                  30

Lys Thr Thr Phe Gly Arg Asn Thr Leu Ala Ile Gly Gly Asn Glu Glu
                            35                  40                  45

Ala Ala Arg Leu Ala Gly Val Pro Val Val Arg Thr Lys Ile Ile Ile
                50                      55                  60

Phe Val Leu Ser Gly Leu Val Ser Ala Ile Ala Gly Ile Ile Leu Ala
            65                      70                  75                  80

Ser Arg Met Thr Ser Gly Gln Pro Met Thr Ser Ile Gly Tyr Glu Leu
                            85                  90                  95

Ile Val Ile Ser Ala Cys Val Leu Gly Gly Val Ser Leu Lys Gly Gly
                            100                 105                 110

Ile Gly Lys Ile Ser Tyr Val Val Ala Gly Ile Leu Ile Leu Gly Thr
                            115                 120                 125

Val Glu Asn Ala Met Asn Leu Leu Asn Ile Ser Pro Phe Ala Gln Tyr
                            130                 135                 140

Val Val Arg Gly Leu Ile Leu Leu Ala Ala Val Ile Phe Asp Arg Tyr
            145                     150                 155                 160

Lys Gln Lys Ala Lys Arg Thr Val
                            165

(2) INFORMATION FOR SEQ ID NO: 3:

(i) SEQUENCE CHARACTERISTICS:
        (A) LENGTH:   266 amino acids
        (B) TYPE:     amino acid
        (D) TOPOLOGY: linear (ii) MOLECULE TYPE:   peptide (xi) SEQUENCE DESCRIPTION: SEQ ID NO: 3:

Val Thr Glu Pro Leu Thr Glu Thr Pro Glu Leu Ser Ala Lys Tyr Ala
            1                   5                   10                  15

Trp Phe Phe Asp Leu Asp Gly Thr Leu Ala Glu Ile Lys Pro His Pro
                            20                  25                  30

Asp Gln Val Val Pro Asp Asn Ile Leu Gln Gly Leu Gln Leu Leu
                        35                  40                  45

Ala Thr Ala Ser Asp Gly Ala Leu Ala Leu Ile Ser Gly Arg Ser Met
                50                  55                  60

Val Glu Leu Asp Ala Leu Ala Lys Pro Tyr Arg Phe Pro Leu Ala Gly
            65                      70                  75                  80

Val His Gly Ala Glu Arg Arg Asp Ile Asn Gly Lys Thr His Ile Val
                            85                  90                  95

His Leu Pro Asp Ala Ile Ala Arg Asp Ile Ser Val Gln Leu His Thr
                            100                 105                 110

Val Ile Ala Gln Tyr Pro Gly Ala Glu Leu Glu Ala Lys Gly Met Ala
                            115                 120                 125

Phe Ala Leu His Tyr Arg Gln Ala Pro Gln His Glu Asp Ala Leu Met
                            130                 135                 140

Thr Leu Ala Gln Arg Ile Thr Gln Ile Trp Pro Gln Met Ala Leu Gln
            145                     150                 155                 160

Gln Gly Lys Cys Val Val Glu Ile Lys Pro Arg Gly Thr Ser Lys Gly
                            165                 170                 175

Glu Ala Ile Ala Ala Phe Met Gln Glu Ala Pro Phe Ile Gly Arg Thr
                            180                 185                 190
```

```
Pro Val Phe Leu Gly Asp Asp Leu Thr Asp Glu Ser Gly Phe Ala Val
        195                 200                 205

Val Asn Arg Leu Gly Gly Met Ser Val Lys Ile Gly Thr Gly Ala Thr
    210                 215                 220

Gln Ala Ser Trp Arg Leu Ala Gly Val Pro Asp Val Trp Ser Trp Leu
225                 230                 235                 240

Glu Met Ile Thr Thr Ala Leu Gln Gln Lys Arg Glu Asn Asn Arg Ser
                245                 250                 255

Asp Asp Tyr Glu Ser Phe Ser Arg Ser Ile
        260                 265

(2) INFORMATION FOR SEQ ID NO: 4:

(i) SEQUENCE CHARACTERISTICS:
        (A) LENGTH:    475 amino acids
        (B) TYPE:      amino acid
        (D) TOPOLOGY:  linear (ii) MOLECULE TYPE:   peptide (xi) SEQUENCE DESCRIPTION: SEQ ID NO: 4:

Met Thr Met Ser Arg Leu Val Val Ser Asn Arg Ile Ala Pro Pro
1               5                   10                  15

Asp Glu His Ala Ala Ser Ala Gly Gly Leu Ala Val Gly Ile Leu Gly
            20                  25                  30

Ala Leu Lys Ala Ala Gly Gly Leu Trp Phe Gly Trp Ser Gly Glu Thr
        35                  40                  45

Gly Asn Glu Asp Gln Pro Leu Lys Lys Val Lys Lys Gly Asn Ile Thr
50                  55                  60

Trp Ala Ser Phe Asn Leu Ser Glu Gln Asp Leu Asp Glu Tyr Tyr Asn
65                  70                  75                  80

Gln Phe Ser Asn Ala Val Leu Trp Pro Ala Phe His Tyr Arg Leu Asp
                85                  90                  95

Leu Val Gln Phe Gln Arg Pro Ala Trp Asp Gly Tyr Leu Arg Val Asn
            100                 105                 110

Ala Leu Leu Ala Asp Lys Leu Leu Pro Leu Leu Gln Asp Asp Asp Ile
        115                 120                 125

Ile Trp Ile His Asp Tyr His Leu Leu Pro Phe Ala His Glu Leu Arg
    130                 135                 140

Lys Arg Gly Val Asn Asn Arg Ile Gly Phe Phe Leu His Ile Pro Phe
145                 150                 155                 160

Pro Thr Pro Glu Ile Phe Asn Ala Leu Pro Thr Tyr Asp Thr Leu Leu
                165                 170                 175

Glu Gln Leu Cys Asp Tyr Asp Leu Leu Gly Phe Gln Thr Glu Asn Asp
            180                 185                 190

Arg Leu Ala Phe Leu Asp Cys Leu Ser Asn Leu Thr Arg Val Thr Thr
        195                 200                 205

Arg Ser Ala Lys Ser His Thr Ala Trp Gly Lys Ala Phe Arg Thr Glu
    210                 215                 220

Val Tyr Pro Ile Gly Ile Glu Pro Lys Glu Ile Ala Lys Gln Ala Ala
225                 230                 235                 240

Gly Pro Leu Pro Pro Lys Leu Ala Gln Leu Lys Ala Glu Leu Lys Asn
                245                 250                 255

Val Gln Asn Ile Phe Ser Val Glu Arg Leu Asp Tyr Ser Lys Gly Leu
            260                 265                 270
```

-continued

```
Pro Glu Arg Phe Leu Ala Tyr Glu Ala Leu Leu Glu Lys Tyr Pro Gln
            275                 280                 285

His His Gly Lys Ile Arg Tyr Thr Gln Ile Ala Pro Thr Ser Arg Gly
        290                 295                 300

Asp Val Gln Ala Tyr Gln Asp Ile Arg His Gln Leu Glu Asn Glu Ala
305                 310                 315                 320

Gly Arg Ile Asn Gly Lys Tyr Gly Gln Leu Gly Trp Thr Pro Leu Tyr
                325                 330                 335

Tyr Leu Asn Gln His Phe Asp Arg Lys Leu Leu Met Lys Ile Phe Arg
            340                 345                 350

Tyr Ser Asp Val Gly Leu Val Thr Pro Leu Arg Asp Gly Met Asn Leu
        355                 360                 365

Val Ala Lys Glu Tyr Val Ala Ala Gln Asp Pro Ala Asn Pro Gly Val
    370                 375                 380

Leu Val Leu Ser Gln Phe Ala Gly Ala Ala Asn Glu Leu Thr Ser Ala
385                 390                 395                 400

Leu Ile Val Asn Pro Tyr Asp Arg Asp Glu Val Ala Ala Ala Leu Asp
                405                 410                 415

Arg Ala Leu Thr Met Ser Leu Ala Glu Arg Ile Ser Arg His Ala Glu
            420                 425                 430

Met Leu Asp Val Ile Val Lys Asn Asp Ile Asn His Trp Gln Glu Cys
        435                 440                 445

Phe Ile Ser Asp Leu Lys Gln Ile Val Pro Arg Ser Ala Glu Ser Gln
    450                 455                 460

Gln Arg Asp Lys Val Ala Thr Phe Pro Lys Leu
465                 470                 475

(2) INFORMATION FOR SEQ ID NO: 5:

(i) SEQUENCE CHARACTERISTICS:
        (A) LENGTH:    700 amino acids
        (B) TYPE:      amino acid
        (D) TOPOLOGY:  linear (ii) MOLECULE TYPE:    peptide (xi) SEQUENCE DESCRIPTION: SEQ ID NO: 5:

Gly Ala Met Asp Lys Leu His Xaa Gly Ser Lys Thr His Val Leu Leu
1               5                   10                  15

Xaa Val Cys Ile Tyr Arg Glu Arg Leu Arg Arg Thr Arg Val Val Gly
            20                  25                  30

Arg Asp Xaa Leu Thr Trp Xaa Ser Tyr Leu Val Asn Xaa Val Ser Val
        35                  40                  45

Ser Phe Leu Leu Glu Gln Ala Arg Ser Xaa Val Ser Asn Lys Ala Gly
    50                  55                  60

Xaa Gln Thr Arg Tyr Ser His Thr Asp Leu Leu Arg His Arg Thr Met
65                  70                  75                  80

Thr Thr Asp Asn Ala Lys Ala Gln Leu Thr Ser Ser Ser Gly Gly Asn
                85                  90                  95

Ile Ile Val Val Ser Asn Arg Leu Pro Val Thr Ile Thr Lys Lys Gln
            100                 105                 110

Gln Tyr Gly Thr Val Arg Val Thr Gln Cys Arg Pro Glu Ala Gly His
        115                 120                 125

Gly Val Gly Arg Val Glu Glu Asp Val His Phe Gln Trp Phe Gly Trp
    130                 135                 140

Pro Gly Leu Glu Ile Pro Asp Asp Glu Lys Asp Gln Val Arg Lys Asp
```

-continued

```
            145                 150                 155                 160

Leu Leu Glu Lys Phe Asn Ala Val Pro Ile Phe Leu Ser Asp Glu Ile
                165                 170                 175

Glu Thr Tyr Thr Thr Thr Gly Ser Val Ile Leu Phe Tyr Gly Arg Tyr
            180                 185                 190

Ser Ile Thr Ile Leu Val Arg Ser Ile Ser Thr Arg Met Arg Gly Ser
                195                 200                 205

Asp Asn Ala Lys Ala Gln His Gln Thr Phe Thr Asn Glu Ile Ala Lys
            210                 215                 220

Thr Met Asn His Asn Asp Leu Ile Trp Val His Asp Tyr His Leu Met
225                 230                 235                 240

Leu Val Pro Glu Met Leu Arg Val Lys Ile His Glu Lys Gln Leu Gln
                245                 250                 255

Asn Val Lys Val Gly Trp Phe Leu His Thr Pro Phe Pro Ser Ser Glu
                260                 265                 270

Ile Tyr Arg Ile Leu Pro Val Arg Gln Glu Ile Leu Lys Gly Val Leu
                275                 280                 285

Ser Cys Asp Leu Val Gly Phe His Thr Tyr Asp Tyr Ala Arg His Phe
                290                 295                 300

Leu Ser Ser Val Gln Arg Val Leu Asn Val Asn Thr Leu Pro Asn Gly
305                 310                 315                 320

Val Glu Tyr Arg Ala Asp Ser Leu Thr Xaa Gly Pro Ser Leu Ser Val
                325                 330                 335

Ser Thr Trp Thr Ser Ser Pro Met Gly Xaa Lys Arg Asn Pro Tyr Lys
                340                 345                 350

Arg Glu Ser Asn Asn Xaa Arg Lys Leu Ser Arg Ala Ala Arg Ser Xaa
                355                 360                 365

Leu Val Ser Thr Gly Trp Ile Thr Ser Lys Val Cys Pro Gln Lys Leu
370                 375                 380

His Ala Met Glu Val Phe Leu Asn Glu His Pro Glu Trp Arg Gly Lys
385                 390                 395                 400

Val Val Leu Val Gln Val Ala Val Pro Ser Arg Gly Asp Val Glu Glu
                405                 410                 415

Tyr Gln Tyr Leu Arg Ser Val Val Asn Glu Leu Val Gly Arg Ile Thr
                420                 425                 430

Val Ser Ser Val Leu Trp Asn Ser Ser Pro Ser Ile Ser Cys Thr Ser
                435                 440                 445

Leu Tyr His Leu Lys Ser Xaa Phe Arg Tyr Met Leu Xaa Ala Met Phe
                450                 455                 460

Val Trp Ser Arg Pro Pro Val Met Val Xaa Thr Trp Phe Pro Thr Asn
465                 470                 475                 480

Ile Leu Leu Ala Lys Lys Lys Arg Lys Val Pro Xaa Ser Xaa Val Ser
                485                 490                 495

Ser Gln Val Pro His Asn Pro Xaa Met Val Leu Leu Xaa Ile Leu
                500                 505                 510

Gly Thr Pro Met Ile Phe Leu Met Pro Ser Thr Arg Pro Xaa Leu Cys
                515                 520                 525

Pro Met Xaa Arg Lys Lys Leu Thr Gly Lys Asn Phe Thr Asn Thr Ser
                530                 535                 540

Leu Asn Thr Leu Leu Pro Ser Gly Val Lys Ile Ser Ser Met Asn Tyr
545                 550                 555                 560

Thr Val His His Gln Ala Gln Gln Ala Pro Leu Pro Pro Lys Thr Asp
                565                 570                 575
```

-continued

```
Glu Pro Asp Ala Lys Xaa Asp Asp Arg Leu Phe Leu Val Arg Phe Ser
                580                 585                 590

Leu Pro Ser Leu Leu Phe Thr Phe Phe Thr Thr Leu Tyr Lys Ile Ile
            595                 600                 605

Xaa Met Thr Xaa Leu Lys Arg His Thr Ser Ser Pro Ile Arg Xaa Arg
        610                 615                 620

Leu Ser Val Ala Leu Leu Leu Lys Leu Arg Lys Xaa Phe Phe Ser Arg
625                 630                 635                 640

Ile Gly Pro Leu Phe Leu Ser Leu Ser Phe Ser Pro Ala Leu Ile Ser
                645                 650                 655

Ser Ser Lys His His Glu Xaa Lys Glu Lys Gly Asn Gln Glu Lys Lys
            660                 665                 670

Ala Ile Ile Tyr Pro Thr Phe Phe Ile Val Ala Val His Thr Ala
                675                 680                 685

Xaa Arg Arg Tyr Trp Leu His Lys Gln Leu Thr Leu
        690                 695                 700
```

(2) INFORMATION FOR SEQ ID NO: 6:

(i) SEQUENCE CHARACTERISTICS:
        (A) LENGTH:    699 amino acids
        (B) TYPE:    amino acid
        (D) TOPOLOGY:    linear (ii) MOLECULE TYPE:    peptide (xi) SEQUENCE DESCRIPTION: SEQ ID NO: 6:

```
Arg His Gly Gln Thr Ala Leu Arg Phe Xaa Asp Thr Cys Ile Ile Val
1               5                   10                  15

Ser Met Tyr Ile Xaa Arg Glu Ile Lys Ala Tyr Thr Arg Gly Trp Xaa
                20                  25                  30

Arg Leu Ile Asn Leu Val Val Leu Ser Cys Gln Leu Ser Phe Cys Gln
            35                  40                  45

Phe Pro Ser Xaa Thr Ser Thr Gln Leu Ser Lys Gln Gln Ser Arg Leu
        50                  55                  60

Thr Asn Xaa Val Leu Thr Tyr Arg Leu Ile Lys Thr Xaa Asn Tyr Asp
65                  70                  75                  80

Tyr Gly Xaa Arg Xaa Gly Ala Thr Asp Leu Val Phe Arg Gly Xaa His
                85                  90                  95

Tyr Cys Gly Val Gln Gln Ala Ser Arg Asp Asn His Xaa Lys Thr Ala
            100                 105                 110

Val Arg Asp Ser Thr Ser Asp Ala Met Ser Ser Gly Gly Trp Ser Arg
        115                 120                 125

Arg Trp Lys Gly Xaa Arg Arg Thr Leu Ser Val Val Arg Met Ala
130                 135                 140

Trp Ala Arg Asp Ser Xaa Arg Xaa Glu Gly Ser Gly Glu Glu Gly Leu
145                 150                 155                 160

Ala Gly Lys Val Xaa Cys Arg Thr His Leu Pro Glu Arg Xaa Asn Arg
                165                 170                 175

Asp Leu His Tyr Asn Gly Phe Ser Asn Ser Ile Leu Trp Pro Leu Phe
            180                 185                 190

His Tyr His Pro Gly Glu Ile Asn Phe Asp Glu Asn Ala Trp Phe Gly
        195                 200                 205

Xaa Arg Xaa Gly Ala Thr Pro Asp Val His Gln Arg Asp Cys Xaa Asp
210                 215                 220
```

```
Tyr Glu Pro Xaa Arg Phe Asn Leu Gly Ala Xaa Leu Pro Phe Asp Val
225                 230                 235                 240

Gly Ser Gly Asn Val Glu Ser Gln Asp Ser Arg Glu Ala Thr Ala Lys
            245                 250                 255

Arg Xaa Gly Arg Val Val Pro Ala His Thr Ile Pro Phe Glu Xaa Asn
        260                 265                 270

Leu Gln Asn Leu Thr Cys Gln Thr Arg Asp Phe Glu Gly Cys Phe Glu
    275                 280                 285

Leu Xaa Phe Ser Arg Val Pro His Ile Arg Leu Cys Lys Thr Phe Leu
    290                 295                 300

Val Phe Arg Ala Lys Ser Ala Xaa Arg Glu His Ile Ala Xaa Trp Gly
305                 310                 315                 320

Gly Ile Gln Gly Arg Phe Val Asn Val Gly Ala Phe Pro Ile Gly Ile
            325                 330                 335

Asp Val Asp Lys Phe Thr Asp Gly Leu Lys Lys Glu Ser Val Gln Lys
        340                 345                 350

Arg Ile Gln Gln Leu Lys Glu Thr Phe Lys Gly Cys Lys Ile Ile Val
    355                 360                 365

Gly Val Asp Arg Leu Asp Tyr Ile Lys Gly Val Pro Ser Glu Val Ala
    370                 375                 380

Arg His Gly Ser Val Ser Glu Arg Ala Ser Arg Met Glu Gly Gln Gly
385                 390                 395                 400

Cys Ser Gly Thr Gly Cys Ser Ala Lys Ser Trp Arg Cys Gly Arg Val
            405                 410                 415

Pro Ile Phe Lys Ile Cys Gly Gln Xaa Val Gly Arg Xaa Asn His Gly
        420                 425                 430

Gln Phe Gly Thr Val Glu Phe Val Pro Ile His Phe Met His Lys Ser
    435                 440                 445

Ile Pro Phe Glu Glu Leu Ile Ser Leu Tyr Ala Val Ser Asp Val Cys
    450                 455                 460

Leu Val Ser Ser Thr Arg Asp Gly Met Asn Leu Val Ser Tyr Glu Tyr
465                 470                 475                 480

Ile Ala Cys Gln Glu Glu Lys Lys Gly Ser Leu Ile Leu Ser Glu Phe
            485                 490                 495

Thr Gly Ala Ala Gln Ser Leu Asn Gly Ala Ile Ile Val Asn Pro Trp
        500                 505                 510

Asn Thr Asp Asp Leu Ser Asp Ala Ile Asn Glu Ala Leu Thr Leu Pro
    515                 520                 525

Asp Val Lys Lys Glu Val Asn Trp Glu Lys Leu Tyr Lys Tyr Ile Ser
    530                 535                 540

Lys Tyr Thr Ser Ala Phe Trp Gly Glu Asn Phe Val His Glu Leu Tyr
545                 550                 555                 560

Ser Thr Ser Ser Ser Ser Thr Ser Ser Ser Ala Thr Lys Asn Xaa Xaa
            565                 570                 575

Thr Arg Cys Lys Met Arg Arg Ser Ser Ile Pro Gly Pro Val Phe Ser
        580                 585                 590

Ala Leu Ser Ser Ile His Phe Phe Tyr Tyr Phe Ile Xaa Asn Tyr Ile
    595                 600                 605

Asn Asp Ile Thr Glu Thr Pro His Val Leu Ser Tyr Ser Leu Thr Pro
    610                 615                 620

Val Cys Ser Ala Val Thr Glu Ala Ala Gln Val Val Phe Phe Thr Tyr
625                 630                 635                 640

Arg Pro Ser Phe Ser Leu Ser Phe Phe Leu Ser Arg Ala Asp Leu Phe
```

-continued

```
                        645                     650                     655

Phe Glu Thr Ser Xaa Ile Lys Arg Lys Arg Lys Ser Arg Lys Lys Ser
                660                     665                 670

His Asn Leu Ser His Ile Phe Phe Tyr Cys Arg Cys Ser His Arg Ile
                675                     680                 685

Thr Lys Ile Leu Ala Thr Xaa Thr Ile Asp Ile
        690                     695
```